United States Patent
Sharkey et al.

(10) Patent No.: US 6,380,160 B1
(45) Date of Patent: Apr. 30, 2002

(54) GP130 LACKING THE TRANSMEMBRANE DOMAIN

(75) Inventors: Andrew Sharkey; Stephen Kevin Smith, both of Cambridge; Kimberley Anne Dellow, London, all of (GB)

(73) Assignee: Applied Research Systems ARS Holding NV., Curacao (NL)

(*) Notice: Subject to any disclaimer, the term of this patent is extended or adjusted under 35 U.S.C. 154(b) by 0 days.

(21) Appl. No.: 09/312,611

(22) Filed: May 17, 1999

Related U.S. Application Data

(62) Division of application No. 08/825,558, filed on Mar. 19, 1997, now Pat. No. 5,965,724, which is a continuation of application No. PCT/GB95/02243, filed on Sep. 21, 1995, now abandoned.

(30) Foreign Application Priority Data

Sep. 21, 1994 (GB) .............................................. 9419021

(51) Int. Cl.$^7$ ...................... A61K 38/17; C07K 14/715; C12N 15/12
(52) U.S. Cl. .......................... 514/12; 530/350; 536/23.5
(58) Field of Search .......................... 530/350; 514/12; 536/23.5

(56) References Cited

U.S. PATENT DOCUMENTS

| | | | |
|---|---|---|---|
| 5,132,403 A | 7/1992 | Kishimoto | |
| 5,223,611 A | 6/1993 | Kishimoto | |
| 5,426,048 A | 6/1995 | Gearing | |
| 5,783,672 A | 7/1998 | Mosley et al. | |

FOREIGN PATENT DOCUMENTS

| | | |
|---|---|---|
| EP | 0 411 946 A2 | 2/1991 |
| JP | 06-22786 | 2/1994 |
| WO | WO 93/10151 | 5/1993 |
| WO | WO 95/33059 | 12/1995 |
| WO | WO 96/09382 | 3/1996 |

OTHER PUBLICATIONS

Adamson, E.D., "Activities of Growth Factors in Preimplantation Embryos," *J. Cell. Biochem.* 53:280–287 (Dec. 1993).
Geisterfer M. et al., "Cytokines Oncostatin M and Interleukin 1 Regulate the Expression of the IL–6 Receptor (gp80 and gp130)," *Cytokine* 7:503–509 (Aug. 1995).
Harvey, M.B. and Kaye, P.L., "Insulin–Like Growth Factor–1 Stimulates Growth of Mouse Preimplantation Embryos in vitro," *Mol. Reprod. Dev.* 31:195–199 (Mar. 1992).
Hibi M. et al., "Molecular Cloning and Expression of an IL–6 Signal Transducer, gp130," *Cell* 63:1149–57 (Dec. 1990).
Hill, J.A. et al., "Products of Activated Lymphocytes and Macrophages Inhibit Mouse Embryo Development in vitro," *J. Immunol.* 139:2250–2254 (Oct. 1987).
Lachapelle, M.H. et al., "Embryonic Resistance to Tumor Necrosis Factor–α Mediated Cytotoxicity: Novel Mechanism Underlying Maternal Immunological Tolerance to the Fetal Allograft," *Human Reproduction* 8:1032–1038 (Jul. 1993).
Narazaki, M. et al., "Soluble Forms of the Interleukin–6 Signal–Transducing Receptor Component gp130 in Human Serum Possessing a Potential to Inhibit Signals Through Membrane–Anchored gp130," *Blood* 82:1120–1126 (Aug. 1993).
Pampfer, S. et al., "Expression of Tumor Necrosis Factor–α (TNFα) Receptors and Selective Effect of TNFα on the Inner Cell Mass in Mouse Blastocysts," *Endocrinology* 134:206–212 (Jan. 1994).
Rappolee, D.A. et al., "Developmental Expression of PDGF, TGF–α, and TGF–β Genes in Preimplantation Mouse Embryos," *Science* 241:1823–1825 (Sep. 1988).
Schultz, G.A. and Heyner, S., "Gene Expression in Pre–implantation Mammalian Embryos," *Mutation Research* 296:17–31 (Dec. 1992).
Sharkey, A.M. et al., Stage–specific Expression of Cytokine and Receptor Messenger Ribonucleic Acids in Human Pre-implantation Embryos, *Biol. Reprod.* 53:974–981 (Oct. 1995).
Taga, T. et al., "Functional Inhibition of Hematopoietic and Neurotrophic Cytokines by Blocking the Interleukin 6 Signal Transducer gp130," *Proc. Natl. Acad. Sci. USA* 89:10998–11001 (Nov. 1992).
Watson, A.J. et al., "A Growth Factor Phenotype Map for Ovine Preimplantation Development," *Biol. Reprod.* 50:725–733 (Apr. 1994).
Witkin, S.S. et al., "Tumor Necrosis Factor is Present in Maternal Sera and Embryo Culture Fluids During in vitro Fertilization," *J. Reprod. Immunol.* 19:85–93 (Jan. 1991).
Yasukawa, K. et al., "Association of Recombinant Soluble IL–6 Signal Transducer, gp130, with a Complex of IL 6 and Soluble IL–6 Receptor, and Establishment of an ELISA for Soluble gp130," *Immunology Letters* 31:123–130 (Feb. 1992).
Zolti, M. et al., "Cytokine involvement in oocytes and early embryos," *Fertility and Sterility* 56:265–272 (Aug. 1991).
English Language abstract of Japanese Patent No. 06–22786 (document AL1), *Patent Abstracts of Japan* 18:c–1194 (Apr. 1994).
Copy of the International Search Report for International Application No. PCT/GB95/02243.

*Primary Examiner*—Lorraine Spector
*Assistant Examiner*—Claire M. Kaufman
(74) *Attorney, Agent, or Firm*—Sterne, Kessler, Goldstein & Fox P.L.L.C.

(57) ABSTRACT

A novel splice-variant of gp130 is disclosed, together with the DNA sequence coding for it, pharmaceutical compositions comprising it and its use in ensuring the correct development of pre-implantation embryos.

9 Claims, 11 Drawing Sheets

FIG. 1A

```
                                               5
                            Met Leu Thr Leu Gln Thr Trp
                            ATG TTG ACG TTG CAG ACT TGG 10                      15                     20
Val Val Gln Ala Leu Phe Ile Phe Leu Thr Thr Glu Ser Thr
GTA GTG CAA GCC TTG TTT ATT TTC CTC ACC ACT GAA TCT ACA 25                      30                     35
Gly Glu Leu Leu Asp Pro Cys Gly Tyr Ile Ser Pro Glu Ser
GGT GAA CTT CTA GAT CCA TGT GGT TAT ATC AGT CCT GAA TCT 40                      45
Pro Val Val Gln Leu His Ser Asn Phe Thr Ala Val Cys Val
CCA GTT GTA CAA CTT CAT TCT AAT TTC ACT GCA GTT TGT GTG 50                      55                      60
Leu Lys Glu Lys Cys Met Asp Tyr Phe His Val Asn Ala Asn
CTA AAG GAA AAA TGT ATG GAT TAT TTT CAT GTA AAT GCT AAT 65                      70                     75
Tyr Ile Val Trp Lys Thr Asn His Phe Thr Ile Pro Lys Glu
TAC ATT GTC TGG AAA ACA AAC CAT TTT ACT ATT CCT AAG GAG 80                      85                     90
Gln Tyr Thr Ile Ile Asn Arg Thr Ala Ser Ser Val Thr Phe
CAA TAT ACT ATC ATA AAC AGA ACA GCA TCC AGT GTC ACC TTT 95                      100                    105
Thr Asp Ile Ala Ser Leu Asn Ile Gln Leu Thr Cys Asn Ile
ACA GAT ATA GCT TCA TTA AAT ATT CAG CTC ACT TGC AAC ATT 110                     115
Leu Thr Phe Gly Gln Leu Glu Gln Asn Val Tyr Gly Ile Thr
CTT ACA TTC GGA CAG CTT GAA CAG AAT GTT TAT GGA ATC ACA 120                     125                     130
Ile Ile Ser Gly Leu Pro Pro Glu Lys Pro Lys Asn Leu Ser
ATA ATT TCA GGC TTG CCT CCA GAA AAA CCT AAA AAT TTG AGT
```

FIG. 1B

```
              135                              140                              145
     Cys  Ile  Val  Asn  Glu  Gly  Lys  Lys  Met  Arg  Cys  Glu  Trp  Asp
     TGC  ATT  GTG  AAC  GAG  GGG  AAG  AAA  ATG  AGG  TGT  GAG  TGG  GAT 150                              155                              160
     Gly  Gly  Arg  Glu  Thr  His  Leu  Glu  Thr  Asn  Phe  Thr  Leu  Lys
     GGT  GGA  AGG  GAA  ACA  CAC  TTG  GAG  ACA  AAC  TTC  ACT  TTA  AAA 165                              170                              175
     Ser  Glu  Trp  Ala  Thr  His  Lys  Phe  Ala  Asp  Cys  Lys  Ala  Lys
     TCT  GAA  TGG  GCA  ACA  CAC  AAG  TTT  GCT  GAT  TGC  AAA  GCA  AAA 180                              185
     Arg  Asp  Thr  Pro  Thr  Ser  Cys  Thr  Val  Asp  Tyr  Ser  Thr  Val
     CGT  GAC  ACC  CCC  ACC  TCA  TGC  ACT  GTT  GAT  TAT  TCT  ACT  GTG 190                              195                              200
     Tyr  Phe  Val  Asn  Ile  Glu  Val  Trp  Val  Glu  Ala  Glu  Asn  Ala
     TAT  TTT  GTC  AAC  ATT  GAA  GTC  TGG  GTA  GAA  GCA  GAG  AAT  GCC 205                              210                              215
     Leu  Gly  Lys  Val  Thr  Ser  Asp  His  Ile  Asn  Phe  Asp  Pro  Val
     CTT  GGG  AAG  GTT  ACA  TCA  GAT  CAT  ATC  AAT  TTT  GAT  CCT  GTA 220                              225                              230
     Tyr  Lys  Val  Lys  Pro  Asn  Pro  Pro  His  Asn  Leu  Ser  Val  Ile
     TAT  AAA  GTG  AAG  CCC  AAT  CCG  CCA  CAT  AAT  TTA  TCA  GTG  ATC 235                              240                              245
     Asn  Ser  Glu  Glu  Leu  Ser  Ser  Ile  Leu  Lys  Leu  Thr  Trp  Thr
     AAC  TCA  GAG  GAA  CTG  TCT  AGT  ATC  TTA  AAA  TTG  ACA  TGG  ACC 250                              255
     Asn  Pro  Ser  Ile  Lys  Ser  Val  Ile  Ile  Leu  Lys  Tyr  Asn  Ile
     AAC  CCA  AGT  ATT  AAG  AGT  GTT  ATA  ATA  CTA  AAA  TAT  AAC  ATT 260                              265                              270
     Gln  Tyr  Arg  Thr  Lys  Asp  Ala  Ser  Thr  Trp  Ser  Gln  Ile  Pro
     CAA  TAT  AGG  ACC  AAA  GAT  GCC  TCA  ACT  TGG  AGC  CAG  ATT  CCT 275                              280                              285
     Pro  Glu  Asp  Thr  Ala  Ser  Thr  Arg  Ser  Ser  Phe  Thr  Val  Gln
     CCT  GAA  GAC  ACA  GCA  TCC  ACC  CGA  TCT  TCA  TTC  ACT  GTC  CAA 290                              295                              300
     Asp  Leu  Lys  Pro  Phe  Thr  Glu  Tyr  Val  Phe  Arg  Ile  Arg  Cys
     GAC  CTT  AAA  CCT  TTT  ACA  GAA  TAT  GTG  TTT  AGG  ATT  CGC  TGT
```

FIG. 1C

```
                     305                              310                              315
   Met Lys Glu Asp Gly Lys Gly Tyr Trp Ser Asp Trp Ser Glu
   ATG AAG GAA GAT GGT AAG GGA TAC TGG AGT GAC TGG AGT GAA 320                              325
   Glu Ala Ser Gly Ile Thr Tyr Glu Asp Arg Pro Ser Lys Ala
   GAA GCA AGT GGG ATC ACC TAT GAA GAT AGA CCA TCT AAA GCA 330                              335                              340
   Pro Ser Phe Trp Tyr Lys Ile Asp Pro Ser His Thr Gln Gly
   CCA AGT TTC TGG TAT AAA ATA GAT CCA TCC CAT ACT CAA GGC 345                              350                              355
   Tyr Arg Thr Val Gln Leu Val Trp Lys Thr Leu Pro Pro Phe
   TAC AGA ACT GTA CAA CTC GTG TGG AAG ACA TTG CCT CCT TTT 360                              365                              370
   Glu Ala Asn Gly Lys Ile Leu Asp Tyr Glu Val Thr Leu Thr
   GAA GCC AAT GGA AAA ATC TTG GAT TAT GAA GTG ACT CTC ACA 375                              380                              385
   Arg Trp Lys Ser His Leu Gln Asn Tyr Thr Val Asn Ala Thr
   AGA TGG AAA TCA CAT TTA CAA AAT TAC ACA GTT AAT GCC ACA 390                              395
   Lys Leu Thr Val Asn Leu Thr Asn Asp Arg Tyr Leu Ala Thr
   AAA CTG ACA GTA AAT CTC ACA AAT GAT CGC TAT CTA GCA ACC 400                              405                              410
   Leu Thr Val Arg Asn Leu Val Gly Lys Ser Asp Ala Ala Val
   CTA ACA GTA AGA AAT CTT GTT GGC AAA TCA GAT GCA GCT GTT 415                              420                              425
   Leu Thr Ile Pro Ala Cys Asp Phe Gln Ala Thr His Pro Val
   TTA ACT ATC CCT GCC TGT GAC TTT CAA GCT ACT CAC CCT GTA 430                              435                              440
   Met Asp Leu Lys Ala Phe Pro Lys Asp Asn Met Leu Trp Val
   ATG GAT CTT AAA GCA TTC CCC AAA GAT AAC ATG CTT TGG GTG 445                              450                              455
   Glu Trp Thr Thr Pro Arg Glu Ser Val Lys Lys Tyr Ile Leu
   GAA TGG ACT ACT CCA AGG GAA TCT GTA AAG AAA TAT ATA CTT 460                              465
   Glu Trp Cys Val Leu Ser Asp Lys Ala Pro Cys Ile Thr Asp
   GAG TGG TGT GTG TTA TCA GAT AAA GCA CCC TGT ATC ACA GAC
```

FIG. 1D

```
     470                         475                         480
Trp  Gln  Gln  Glu  Asp  Gly  Thr  Val  His  Arg  Thr  Tyr  Leu  Arg
TGG  CAA  CAA  GAA  GAT  GGT  ACC  GTG  CAT  CGC  ACC  TAT  TTA  AGA 485                         490                         495
Gly  Asn  Leu  Ala  Glu  Ser  Lys  Cys  Tyr  Leu  Ile  Thr  Val  Thr
GGG  AAC  TTA  GCA  GAG  AGC  AAA  TGC  TAT  TTG  ATA  ACA  GTT  ACT 500                         505                         510
Pro  Val  Tyr  Ala  Asp  Gly  Pro  Gly  Ser  Pro  Glu  Ser  Ile  Lys
CCA  GTA  TAT  GCT  GAT  GGA  CCA  GGA  AGC  CCT  GAA  TCC  ATA  AAG 515                         520                         525
Ala  Tyr  Leu  Lys  Gln  Ala  Pro  Pro  Ser  Lys  Gly  Pro  Thr  Val
GCA  TAC  CTT  AAA  CAA  GCT  CCA  CCT  TCC  AAA  GGA  CCT  ACT  GTT 530                         535
Arg  Thr  Lys  Lys  Val  Gly  Lys  Asn  Glu  Ala  Val  Leu  Glu  Trp
CGG  ACA  AAA  AAA  GTA  GGG  AAA  AAC  GAA  GCT  GTC  TTA  GAG  TGG 540                         545                         550
Asp  Gln  Leu  Pro  Val  Asp  Val  Gln  Asn  Gly  Phe  Ile  Arg  Asn
GAC  CAA  CTT  CCT  GTT  GAT  GTT  CAG  AAT  GGA  TTT  ATC  AGA  AAT 555                         560                         565
Tyr  Thr  Ile  Phe  Tyr  Arg  Thr  Ile  Ile  Gly  Asn  Glu  Thr  Ala
TAT  ACT  ATA  TTT  TAT  AGA  ACC  ATC  ATT  GGA  AAT  GAA  ACT  GCT 570                         575                         580
Val  Asn  Val  Asp  Ser  Ser  His  Thr  Glu  Tyr  Thr  Leu  Ser  Ser
GTG  AAT  GTG  GAT  TCT  TCC  CAC  ACA  GAA  TAT  ACA  TTG  TCC  TCT 585                         590                         595
Leu  Thr  Ser  Asp  Thr  Leu  Tyr  Met  Val  Arg  Met  Ala  Ala  Tyr
TTG  ACT  AGT  GAC  ACA  TTG  TAC  ATG  GTA  CGA  ATG  GCA  GCA  TAC 600                         605
Thr  Asp  Glu  Gly  Gly  Lys  Asp  Gly  Pro  Glu  Phe  Thr  Phe  Thr
ACA  GAT  GAA  GGT  GGG  AAG  GAT  GGT  CCA  GAA  TTC  ACT  TTT  ACT 610                         615                         620
Thr  Pro  Lys  Phe  Glu  Leu  Lys  Asn  Thr  Ser  Gly  Leu  Met  Phe
ACC  CCA  AAG  TTT  GAA  TTA  AAA  AAC  ACA  TCT  GGC  CTA  ATG  TTC 625                         630                         635
Gln  Ile  Leu  Gln  Arg  Val  Ile  Leu  Pro  Ser  Gly  His  Leu  Thr
CAG  ATC  CTT  CAA  AGA  GTC  ATA  TTG  CCC  AGT  GGT  CAC  CTC  ACA 640                         645                         650
Leu  Leu  Gln  Gly  Thr  Ile  Leu  Ile  Gln  Lys  Ile  Lys  Cys  Ile
CTC  CTC  CAA  GGC  ACA  ATT  TTA  ATT  CAA  AAG  ATC  AAA  TGT  ATT

655
Gln  Met  Ala  Ile  Ser  Leu  Met
CAG  ATG  GCA  ATT  TCA  CTG  ATG  TAA
```

FIG. 2A

|     |     |     |     | 5   |     |     |
| --- | --- | --- | --- | --- | --- | --- |
| Met | Leu | Thr | Leu | Gln | Thr | Trp |
| ATG | TTG | ACG | TTG | CAG | ACT | TGG |

|     | 10  |     |     |     | 15  |     |     |     | 20  |     |     |
| --- | --- | --- | --- | --- | --- | --- | --- | --- | --- | --- | --- |
| Val | Val | Gln | Ala | Leu | Phe | Ile | Phe | Leu | Thr | Thr | Glu | Ser | Thr |
| GTA | GTG | CAA | GCC | TTG | TTT | ATT | TTC | CTC | ACC | ACT | GAA | TCT | ACA |

|     |     | 25  |     |     |     | 30  |     |     |     | 35  |
| --- | --- | --- | --- | --- | --- | --- | --- | --- | --- | --- |
| Gly | Glu | Leu | Leu | Asp | Pro | Cys | Gly | Tyr | Ile | Ser | Pro | Glu | Ser |
| GGT | GAA | CTT | CTA | GAT | CCA | TGT | GGT | TAT | ATC | AGT | CCT | GAA | TCT |

|     |     |     | 40  |     |     |     | 45  |     |     |     |
| --- | --- | --- | --- | --- | --- | --- | --- | --- | --- | --- |
| Pro | Val | Val | Gln | Leu | His | Ser | Asn | Phe | Thr | Ala | Val | Cys | Val |
| CCA | GTT | GTA | CAA | CTT | CAT | TCT | AAT | TTC | ACT | GCA | GTT | TGT | GTG |

| 50  |     |     |     | 55  |     |     |     | 60  |     |     |     |
| --- | --- | --- | --- | --- | --- | --- | --- | --- | --- | --- | --- |
| Leu | Lys | Glu | Lys | Cys | Met | Asp | Tyr | Phe | His | Val | Asn | Ala | Asn |
| CTA | AAG | GAA | AAA | TGT | ATG | GAT | TAT | TTT | CAT | GTA | AAT | GCT | AAT |

|     | 65  |     |     |     | 70  |     |     |     | 75  |     |     |
| --- | --- | --- | --- | --- | --- | --- | --- | --- | --- | --- | --- |
| Tyr | Ile | Val | Trp | Lys | Thr | Asn | His | Phe | Thr | Ile | Pro | Lys | Glu |
| TAC | ATT | GTC | TGG | AAA | ACA | AAC | CAT | TTT | ACT | ATT | CCT | AAG | GAG |

|     |     | 80  |     |     |     | 85  |     |     |     | 90  |     |
| --- | --- | --- | --- | --- | --- | --- | --- | --- | --- | --- | --- |
| Gln | Tyr | Thr | Ile | Ile | Asn | Arg | Thr | Ala | Ser | Ser | Val | Thr | Phe |
| CAA | TAT | ACT | ATC | ATA | AAC | AGA | ACA | GCA | TCC | AGT | GTC | ACC | TTT |

|     |     |     | 95  |     |     |     | 100 |     |     |     | 105 |
| --- | --- | --- | --- | --- | --- | --- | --- | --- | --- | --- | --- |
| Thr | Asp | Ile | Ala | Ser | Leu | Asn | Ile | Gln | Leu | Thr | Cys | Asn | Ile |
| ACA | GAT | ATA | GCT | TCA | TTA | AAT | ATT | CAG | CTC | ACT | TGC | AAC | ATT |

|     |     |     |     | 110 |     |     |     |     | 115 |     |     |
| --- | --- | --- | --- | --- | --- | --- | --- | --- | --- | --- | --- |
| Leu | Thr | Phe | Gly | Gln | Leu | Glu | Gln | Asn | Val | Tyr | Gly | Ile | Thr |
| CTT | ACA | TTC | GGA | CAG | CTT | GAA | CAG | AAT | GTT | TAT | GGA | ATC | ACA |

| 120 |     |     |     |     | 125 |     |     |     | 130 |     |     |     |
| --- | --- | --- | --- | --- | --- | --- | --- | --- | --- | --- | --- | --- |
| Ile | Ile | Ser | Gly | Leu | Pro | Pro | Glu | Lys | Pro | Lys | Asn | Leu | Ser |
| ATA | ATT | TCA | GGC | TTG | CCT | CCA | GAA | AAA | CCT | AAA | AAT | TTG | AGT |

FIG. 2B

```
         135                         140                         145
Cys Ile Val Asn Glu Gly Lys Lys Met Arg Cys Glu Trp Asp
TGC ATT GTG AAC GAG GGG AAG AAA ATG AGG TGT GAG TGG GAT 150                         155                         160
Gly Gly Arg Glu Thr His Leu Glu Thr Asn Phe Thr Leu Lys
GGT GGA AGG GAA ACA CAC TTG GAG ACA AAC TTC ACT TTA AAA 165                         170                         175
Ser Glu Trp Ala Thr His Lys Phe Ala Asp Cys Lys Ala Lys
TCT GAA TGG GCA ACA CAC AAG TTT GCT GAT TGC AAA GCA AAA 180                         185
Arg Asp Thr Pro Thr Ser Cys Thr Val Asp Tyr Ser Thr Val
CGT GAC ACC CCC ACC TCA TGC ACT GTT GAT TAT TCT ACT GTG 190                         195                         200
Tyr Phe Val Asn Ile Glu Val Trp Val Glu Ala Glu Asn Ala
TAT TTT GTC AAC ATT GAA GTC TGG GTA GAA GCA GAG AAT GCC 205                         210                         215
Leu Gly Lys Val Thr Ser Asp His Ile Asn Phe Asp Pro Val
CTT GGG AAG GTT ACA TCA GAT CAT ATC AAT TTT GAT CCT GTA 220                         225                         230
Tyr Lys Val Lys Pro Asn Pro Pro His Asn Leu Ser Val Ile
TAT AAA GTG AAG CCC AAT CCG CCA CAT AAT TTA TCA GTG ATC 235                         240                         245
Asn Ser Glu Glu Leu Ser Ser Ile Leu Lys Leu Thr Trp Thr
AAC TCA GAG GAA CTG TCT AGT ATC TTA AAA TTG ACA TGG ACC 250                         255
Asn Pro Ser Ile Lys Ser Val Ile Ile Leu Lys Tyr Asn Ile
AAC CCA AGT ATT AAG AGT GTT ATA ATA CTA AAA TAT AAC ATT 260                         265                         270
Gln Tyr Arg Thr Lys Asp Ala Ser Thr Trp Ser Gln Ile Pro
CAA TAT AGG ACC AAA GAT GCC TCA ACT TGG AGC CAG ATT CCT 275                         280                         285
Pro Glu Asp Thr Ala Ser Thr Arg Ser Ser Phe Thr Val Gln
CCT GAA GAC ACA GCA TCC ACC CGA TCT TCA TTC ACT GTC CAA 290                         295                         300
Asp Leu Lys Pro Phe Thr Glu Tyr Val Phe Arg Ile Arg Cys
GAC CTT AAA CCT TTT ACA GAA TAT GTG TTT AGG ATT CGC TGT
```

FIG. 2C

```
                305                        310                        315
    Met Lys Glu Asp Gly Lys Gly Tyr Trp Ser Asp Trp Ser Glu
    ATG AAG GAA GAT GGT AAG GGA TAC TGG AGT GAC TGG AGT GAA 320                        325
    Glu Ala Ser Gly Ile Thr Tyr Glu Asp Arg Pro Ser Lys Ala
    GAA GCA AGT GGG ATC ACC TAT GAA GAT AGA CCA TCT AAA GCA 330                        335                        340
    Pro Ser Phe Trp Tyr Lys Ile Asp Pro Ser His Thr Gln Gly
    CCA AGT TTC TGG TAT AAA ATA GAT CCA TCC CAT ACT CAA GGC 345                        350                        355
    Tyr Arg Thr Val Gln Leu Val Trp Lys Thr Leu Pro Pro Phe
    TAC AGA ACT GTA CAA CTC GTG TGG AAG ACA TTG CCT CCT TTT 360                        365                        370
        Glu Ala Asn Gly Lys Ile Leu Asp Tyr Glu Val Thr Leu Thr
        GAA GCC AAT GGA AAA ATC TTG GAT TAT GAA GTG ACT CTC ACA 375                        380                        385
    Arg Trp Lys Ser His Leu Gln Asn Tyr Thr Val Asn Ala Thr
    AGA TGG AAA TCA CAT TTA CAA AAT TAC ACA GTT AAT GCC ACA 390                        395
        Lys Leu Thr Val Asn Leu Thr Asn Asp Arg Tyr Leu Ala Thr
        AAA CTG ACA GTA AAT CTC ACA AAT GAT CGC TAT CTA GCA ACC 400                        405                        410
    Leu Thr Val Arg Asn Leu Val Gly Lys Ser Asp Ala Ala Val
    CTA ACA GTA AGA AAT CTT GTT GGC AAA TCA GAT GCA GCT GTT 415                        420                        425
    Leu Thr Ile Pro Ala Cys Asp Phe Gln Ala Thr His Pro Val
    TTA ACT ATC CCT GCC TGT GAC TTT CAA GCT ACT CAC CCT GTA 430                        435                        440
        Met Asp Leu Lys Ala Phe Pro Lys Asp Asn Met Leu Trp Val
        ATG GAT CTT AAA GCA TTC CCC AAA GAT AAC ATG CTT TGG GTG 445                        450                        455
        Glu Trp Thr Thr Pro Arg Glu Ser Val Lys Lys Tyr Ile Leu
        GAA TGG ACT ACT CCA AGG GAA TCT GTA AAG AAA TAT ATA CTT 460                        465
        Glu Trp Cys Val Leu Ser Asp Lys Ala Pro Cys Ile Thr Asp
        GAG TGG TGT GTG TTA TCA GAT AAA GCA CCC TGT ATC ACA GAC
```

FIG. 2D

```
                                475                            480
470
Trp Gln Gln Glu Asp Gly Thr Val His Arg Thr Tyr Leu Arg
TGG CAA CAA GAA GAT GGT ACC GTG CAT CGC ACC TAT TTA AGA 485                     490                    495
Gly Asn Leu Ala Glu Ser Lys Cys Tyr Leu Ile Thr Val Thr
GGG AAC TTA GCA GAG AGC AAA TGC TAT TTG ATA ACA GTT ACT 500                    505                    510
Pro Val Tyr Ala Asp Gly Pro Gly Ser Pro Glu Ser Ile Lys
CCA GTA TAT GCT GAT GGA CCA GGA AGC CCT GAA TCC ATA AAG 515                    520                    525
Ala Tyr Leu Lys Gln Ala Pro Pro Ser Lys Gly Pro Thr Val
GCA TAC CTT AAA CAA GCT CCA CCT TCC AAA GGA CCT ACT GGT 530                    535
Arg Thr Lys Lys Val Gly Lys Asn Glu Ala Val Leu Glu Trp
CGG ACA AAA AAA GTA GGG AAA AAC GAA GCT GTC TTA GAG TGG 540                             545                            550
Asp Gln Leu Pro Val Asp Val Gln Asn Gly Phe Ile Arg Asn
GAC CAA CTT CCT GTT GAT GTT CAG AAT GGA TTT ATC AGA AAT 555                             560                    565
Tyr Thr Ile Phe Tyr Arg Thr Ile Ile Gly Asn Glu Thr Ala
TAT ACT ATA TTT TAT AGA ACC ATC ATT GGA AAT GAA ACT GCT 570                            575                    580
Val Asn Val Asp Ser Ser His Thr Glu Tyr Thr Leu Ser Ser
GTG AAT GTG GAT TCT TCC CAC ACA GAA TAT ACA TTG TCC TCT 585                    590                    595
Leu Thr Ser Asp Thr Leu Tyr Met Val Arg Met Ala Ala Tyr
TTG ACT AGT GAC ACA TTG TAC ATG GTA CGA ATG GCA GCA TAC 600                    605
Thr Asp Glu Gly Gly Lys Asp Gly Pro Glu Phe Thr Phe Thr
ACA GAT GAA GGT GGG AAG GAT GGT CCA GAA TTC ACT TTT ACT 610                     615                    620
Thr Pro Lys Phe Ala Gln Gly Glu Ile Glu Ala Ile Val Val
ACC CCA AAG TTT GCT CAA GGA GAA ATT GAA GCC ATA GTC GTG 625                             630                    635
Pro Val Cys Leu Ala Phe Leu Leu Thr Thr Leu Leu Gly Val
CCT GTT TGC TTA GCA TTC CTA TTG ACA ACT CTT CTG GGA GTG 640                            645                    650
Leu Phe Cys Phe Asn Lys Arg Asp Leu Ile Lys Lys His Ile
CTG TTC TGC TTT AAT AAG CGA GAC CTA ATT AAA AAA CAC ATC
```

FIG. 2E

```
                    655                           660                             665
      Trp Pro Asn Val Pro Asp Pro Ser Lys Ser His Ile Ala Gln
      TGG CCT AAT GTT CCA GAT CCT TCA AAG AGT CAT ATT GCC CAG 670                       675
      Trp Ser Pro His Thr Pro Pro Arg His Asn Phe Asn Ser Lys
      TGG TCA CCT CAC ACT CCT CCA AGG CAC AAT TTT AAT TCA AAA 680                       685                       690
      Asp Gln Met Tyr Ser Asp Gly Asn Phe Thr Asp Val Ser Val
      GAT CAA ATG TAT TCA GAT GGC AAT TTC ACT GAT GTA AGT GTT 695                       700                       705
      Val Glu Ile Glu Ala Asn Asp Lys Lys Pro Phe Pro Glu Asp
      GTG GAA ATA GAA GCA AAT GAC AAA AAG CCT TTT CCA GAA GAT 710                       715                       720
      Leu Lys Ser Leu Asp Leu Phe Lys Lys Glu Lys Ile Asn Thr
      CTG AAA TCA TTG GAC CTG TTC AAA AAG GAA AAA ATT AAT ACT 725                         730                       735
      Glu Gly His Ser Ser Gly Ile Gly Gly Ser Ser Cys Met Ser
      GAA GGA CAC AGC AGT GGT ATT GGG GGG TCT TCA TGC ATG TCA 740                         745
      Ser Ser Arg Pro Ser Ile Ser Ser Ser Asp Glu Asn Glu Ser
      TCT TCT AGG CCA AGC ATT TCT AGC AGT GAT GAA AAT GAA TCT 750                       755                       760
      Ser Gln Asn Thr Ser Ser Thr Val Gln Tyr Ser Thr Val Val
      TCA CAA AAC ACT TCG AGC ACT GTC CAG TAT TCT ACC GTG GTA 765                       770                       775
      His Ser Gly Tyr Arg His Gln Val Pro Ser Val Gln Val Phe
      CAC AGT GGC TAC AGA CAC CAA GTT CCG TCA GTC CAA GTC TTC 780                       785                       790
      Ser Arg Ser Glu Ser Thr Gln Pro Leu Leu Asp Ser Glu Glu
      TCA AGA TCC GAG TCT ACC CAG CCC TTG TTA GAT TCA GAG GAG 795                       800                       805
      Arg Pro Glu Asp Leu Gln Leu Val Asp His Val Asp Gly Gly
      CGG CCA GAA GAT CTA CAA TTA GTA GAT CAT GTA GAT GGC GGT
```

FIG. 2F

```
                    810                              815
Asp Gly Ile Leu Pro Arg Gln Gln Tyr Phe Lys Gln Asn Cys
GAT GGT ATT TTG CCC AGG CAA CAG TAC TTC AAA CAG AAC TGC 820                     825                  830
Ser Gln His Glu Ser Ser Pro Asp Ile Ser His Phe Glu Arg
AGT CAG CAT GAA TCC AGT CCA GAT ATT TCA CAT TTT GAA AGG 835                     840                 845
Ser Lys Gln Val Ser Ser Val Asn Glu Glu Asp Phe Val Arg
TCA AAG CAA GTT TCA TCA GTC AAT GAG GAA GAT TTT GTT AGA 850                     855                     860
Leu Lys Gln Gln Ile Ser Asp His Ile Ser Gln Ser Cys Gly
CTT AAA CAG CAG ATT TCA GAT CAT ATT TCA CAA TCC TGT GGA 865                      870                 875
Ser Gly Gln Met Lys Met Phe Gln Glu Val Ser Ala Ala Asp
TCT GGG CAA ATG AAA ATG TTT CAG GAA GTT TCT GCA GCA GAT 880                     885
Ala Phe Gly Pro Gly Thr Glu Gly Gln Val Glu Arg Phe Glu
GCT TTT GGT CCA GGT ACT GAG GGA CAA GTA GAA AGA TTT GAA 890                     895                 900
Thr Val Gly Met Glu Ala Ala Thr Asp Glu Gly Met Pro Lys
ACA GTT GGC ATG GAG GCT GCG ACT GAT GAA GGC ATG CCT AAA 905                     910                 915
Ser Tyr Leu Pro Gln Thr Val Arg Gln Gly Gly Tyr Met Pro
AGT TAC TTA CCA CAG ACT GTA CGG CAA GGC GGC TAC ATG CCT

918
Gln
CAG
```

FIG. 3

FIG. 4

PRIMERS USED FOR RT-PCR

| SPECIFICITY | PRIMER | SEQUENCE 5'→3' | FRAGMENT SIZE (bp) | POSITION ON cDNA | REFERENCE (cDNA SEQUENCE) |
|---|---|---|---|---|---|
| HistRS | EXTERNAL (5'END) | CCGCAGGTCGAGACAGC | | 518-534 | RABEN et al 1992 |
| | EXTERNAL (3'END) | CAAACACCTTCTCGCGAA | | 791-773 | NUCLEIC ACIDS RES |
| | INTERNAL (5'END) | CTTCAGGGAGAGCGCCTGC | | 595-613 | 20:1075-1081 |
| | INTERNAL (3'END) | TCATCAGGACCCAGCTGTGC | 110 | 704-685 | |
| gp130 | EXTERNAL (5'END) | TTGACTAGTGACACATTGTAC | | 1744-1764 | |
| | EXTERNAL (3'END) | TGAAACTTGCTTTGACCTTT | | 2514-2495 | HIBI et al 1990 |
| | INTERNAL (5'END) | GGTACGAATGGCAGCATACA | | 1767-1790 | CELL 63:1149-1157 |
| | INTERNAL (3'END) | CTGGACTGGATTCATGCTGA | 713 | 2480-2461 | |

ID NO:1)
GP130 LACKING THE TRANSMEMBRANE DOMAIN

This application is a divisional of U.S. application Ser. No. 08/825,558, filed Mar. 19, 1997 now U.S. Pat. No. 5.965,724, which [claims priority to] is a continuation of PCT Application No. PCT/GB95/02243, filed Sep. 21, 1995, abandoned.

The present invention relates to a novel human Gp130 protein, DNA sequences coding for this protein, its use in therapy, particularly in in vitro fertilisation, as well as pharmaceutical formulations comprising such a protein.

BACKGROUND OF THE INVENTION

Successful embryo implantation requires correct development of the pre-implantation embryo, resulting in a hatched blastocyst which is able to implant into receptive endometrium. A considerable body of data has been collected which supports the idea that soluble growth factors, if secreted by the uterine epithelium, act directly on the embryo to control this process (Anderson, E. D., *J. Cellular Biochem.*, 53: 280–287 (1993) and Schultz, G. A. and Hevner, S., *Mutat. Res.*, 296: 17–31 (1992))⁻.

In addition, developing embryos have been shown to produce a variety of cytokines which may act in an autocrine fashion on the endometrium to influence its receptivity. Examples of growth factors shown to be produced by human embryos include IL-1, IL-6, CSF-1 and TNF-α (Zolti et al, *Fertil. Steril.*, 56 (1991) 265–272 and Witkin et al, *J. Reprod. Immunol.*, 19 (1991) 85–93). TNF-α has been shown to be present in culture medium of human embryos up to the morula stage, but not that from the blastocyst (Lachappelle et al, *Human Reproduction*, 8: 1032–1038 (1993)). Production of cytokines by the embryo may therefore be regulated in a stage-specific manner.

Data on the possible direct effects of cytokines on embryos have come primarily from experiments in mice where many cytokines have beer shown to affect the development of preimplantation embryos in vitro. RFN-γ and CSF-1, at physiological concentrations, inhibit the number of embryos developing to the blastocyst stage (Hill et al, *J. Immunol.*, 139 (1987) 2250–2254). TNF-α has also been shown to have more subtle effects. Although TNF-α has no apparent effect on rates of blastocyst formation, it appears to specifically inhibit proliferation of cells contributing to the inner cell mass (ICM), which results in blastocysts with a reduced ICM (Pampfer et al, *Endocrinology*, 134: 206–212 (1994)).

Other growth factors also have specific effects on ICM cells. For instance, insulin-like growth factors 1 and 2 stimulate ICM proliferation, whereas leukaemia inhibitory factor (LIF) inhibit their differentiation (Harvey et al, *Mol. Reprod. Dev.*, 31 (1992) 195–199).

As mentioned above, IL-6 is one of the growth factors which has been shown to be produced by human embryos. IL-6 is a protein which controls the proliferation and differentiation of many cell types in mammals, and in addition has a role in the control of the immune system. Binding of IL-6 to IL-6R initiates the association of IL-6R with a third component known as gp130, which actually transmits the signal through the cell membrane (Taga et al, PNAS, 89: 10998–11001). gp130 is a transmembrane protein, i.e. it extends through the membrane and projects into the cytoplasm, thus it has distinct domains. In this way, IL-6 #"signal" transmission is mediated by means of this protein.

EP-A-0411946 discloses a recombinant gp130 protein, as well as DNA sequences coding for such a protein and methods for its cloning.

Yasukawa et al, *Immunology Letters*, 31 (1992) 123–130, disclose a soluble, recombinant form of gp130, produced by removing the transmembrane and cytoplasmic regions of the membrane bound form of the protein.

Narazaki et al, *Blood.*, 82, No 4 (1993) 1120–1126, disclose that soluble forms of gp130 exist and may have potential to inhibit signals normally mediated by transmembrane gp130.

SUMMARY OF THE INVENTION

The present invention relates to a novel human gp130 protein, DNA sequences coding for the protein, use of the protein in therapy, particularly in in vitro fertilization, and pharmaceutical compositions comprising the protein.

The invention further relates to the use of gp130 to antagonize the action of one or more growth factors, wherein the growth factors are IL-6, LIF, CNTF, Oncostatin M and IL-II.

The invention also relates to the use of gp130 to ensure the correct development of pre-implantation embryos.

The invention further relates to pharmaceutical compositions comprising gp130 together with pharmaceutically acceptable excipients.

The invention also relates to a method for antagonizing the action of one or more growth factors in a pre-implantation embryo which comprises the step of administering to the embryo gp130.

DESCRIPTION OF THE PREFERRED EMBODIMENTS

There has now been found a novel form of gp130, lacking the transmembrane portion, which form arises by means of alternative splicing of the sequence coding for the transmembrane gp130. This form of gp130 may bind to complexes of, for example, IL-6 receptor, resulting in a blocking of the association of the complex with transmembrane gp130.

The novel splicing pattern, as well as resulting in loss of the transmembrane domain, also results in a frameshift, leading to 45 new amino acids before an in frame stop codon.

Thus, the present invention provides gp130 which includes the following C-terminal sequence: (SEQ ID NO:1)

Glu Leu Lys Asn Thr Ser Gly Leu Met Phe Gln Ile Leu
Gln Arg Val Ile Leu Pro Ser Gly His Leu Thr Leu Leu
Gln Gly Thr Ile Leu Ile Gln Lys Ile Lys Cys Ile Gln Met
Ala Ile Ser Leu Met or a C-terminal sequence which is substantially homologous thereto.

Preferably, the novel gp130 of he invention has the above-noted sequence from amino ac position 614. In one embodiment the novel gp130 of the invention has a sequence at positions 1–613 substantially homologous to that shown in FIGS. 2A–2F (SEQ ID NO:6)

At the amino acid level, a protein sequence may be regarded as substantially homologous to another protein sequence if a significant number of the constituent amino acids exhibit homology. At least 40%, 50%, 60%, 70%, 80%, 90%, 95% or even 99%, in increasing order of preference, of the amino acids may be homologous.

Thus, activation of the alternative splicing mechanism can result in the production of a novel gp130 in human blastocysts, resulting in inactivation of the effects of, for example, LIF, which in turn ma allow differentiation of the inner cell mass, allowing ICM differentiation to proceed.

Clearly, therefore, the novel gp130 of the invention can be used in the treatment of preimplantation embryos to ensure correct differentiation and development prior to implantation in a subject.

In addition, the invention also provides a DNA sequence coding for a protein of the invention which sequence includes a sequence substantially homologous to: (SEQ ID NO:2)

GAA TTA AAA AAC ACA TCT GGC TA ATG TTC CAG ATC CTT CAA AGA GTC ATA TTG CCC AGT T CAC CTC ACA CTC CTC CAA GGC ACA ATT TTA ATT CAA G ATC AAA TGT ATT CAG ATG GCA ATT TCA CTG ATG TAA

"DNA sequence substantially the same" includes all other nucleic acid sequences which, by virtue of the degeneracy of the genetic code, also code for the given amino acid sequence or which are substantially homologous to such a sequence.

Sequences having substantial homology may be regarded as those which will hybridise to the nucleic acid sequence shown in FIGS. 2A–2F (SEQ ID NO:5) under stringent conditions (for example, at 35 to 65° C. in a salt solution of about 0.9 M).

DNA constructs comprising DNA sequences of the invention form another aspect of the preset invention.

As discussed herein, the protein of the invention is useful in antagonising the action of certain growth factors, thus enabling certain development processes to be "switched on" in preimplantation embryos. Thus, in a further aspect, the present invention provides the use of the protein of the invention in antagonising the action of one or more growth factors, including IL-6, Leukaemia Inhibitory Factor (LIF), Oncostatin Myciliary Neurotrophic Factor (CNTF) and IL-II.

In addition, the invention also provides the use of the protein of the invention in he manufacture of a medicament for use in ensuring correct development in preimplantation embryos. Preferably, the medicament is used to ensure that differentiation of the ICM commences at the correct time.

The medicament is preferably presented in the form of a pharmaceutical formulation comprising the protein of the invention together with one or more pharmaceutically acceptable carriers and/or excipients. Such pharmaceutical formulations form a yet further aspect of the present invention.

A final aspect of the present invention provides a method for antagonising the action of one or more growth factors which comprises the step of treating a pre-implantation embryo with the protein of the present invention, preferably in the form of a pharmaceutical formulation. Preferably the invention provides a method for ensuring correct development of a preimplantation embryo.

The invention will now be described by means of the following examples, which examples should not be construed as in any way limiting the present invention. The examples refer to the following figures which show:

BRIEF DESCRIPTION OF THE DRAWINGS

FIGS. 1A–1D: the sequence of the soluble gp130 (SEQ ID NO:4) and a DNA sequence (SEQ ID NO:3) coding for it;

FIGS. 2A–2F: the sequence of native gp130; (SEQ ID NOS:5 and 6)

FIG. 3: agarose gel showing the products of nested RT-PCR amplification on RNA from human embryos. Each panel shows the products of amplification with primers specific for different cDNA targets. Amplified cDNAs from different embryos were loaded in each lane. Lanes are labelled according to cDNA labels in Table 1 (below). Additional sample, were: lane p, first trimester trophoblast; lane q, cDNA from 200 BeWO cells; lane. r, 10 ng human genomic DNA; and lane s, no input cDNA, as a negative control. DNA molecular weight markers were a 123 base pair ladder loaded in lane i. The sizes of the expected PCR products are shown in bp.

TABLE 1

Human embryo cDNAs and controls
name stage of development a  2 cell
b  3 cell
c  4 cell
d  6 cell
e  8 cell
f  monila
g  blastocyst
h  culture supernatant for a to g
j  three pooled blastocysts
k  culture supernatant for j
l  2 × 6 cell and 1 × 8 cell
m  culture supernatant for 1
n  1 × 4 cell and 1 × 6 cell
o  culture supernatant for n samples a to h are from the same donor.

FIG. 4: primers used for FT-PCR. (SEQ ID NOS:7through 14)

EXAMPLES

Example 1

Embryo Culture and RNA-Extraction

Crypopreserved human embryos which had been fertilised as part of an IVF program were used in this study. These embryos had been donated for research purposes by the parents and this study complied with the requirements of the Human Embryology and Fertilisation Authority, and the local ethical committee. Froze embryos were thawed and cultured in Earles balanced salts medium supplemented with 0.4% human serum albumin (Armour Pharmaceuticals UK), until the required developmental stage, then flash frozen in liquid nitrogen in 5 $\mu$l of culture fluid (and thus lysed by ice crystals). An identical volume of culture supernatant was frozen as a control. Any remaining cumulus cells were removed during routine handling.

Total RNA from first trimester trophoblast was isolated by the method of Chomsczynski and Sacchi, *Anal. Biochem.*, 162: 156–159 (1987) in which frozen tissue is homogenised in 5 ml of buffer containing 4 M guanidinium thiocyanate (Gibco BRL Livingston, Scotland), 25 mM sodium citrate pH 7.0, 0.5 sarcosyl and$_1$ 0.1 M 2-mercaptoethanol. The lysate was acidified by the addition of 0.5 ml of 2 M sodium acetate pH 4, and phenol-chloroform extracted using 5 ml of buffer saturated phenol and 1 ml chloroform-isoamylalcohol (49:1 v/v). The suspension was placed on ice for 15 minutes and centrifuged at 10,000 g for 20 minutes at 4° C. The aqueous phase containing RNA was precipitated, washed twice in 70%. ethanol, dried and resuspended in TE (10 mM Tris-HCl pH 7.4 and 1 mM EDTA). The concentration of RNA was determined spectrophotometrically at 260 nm.

RNA was prepared from single human embryos using a scaled down protocol based on the above procedure. To assist precipitation of the RNA 100 $\mu$g of carrier yeast tRNA (Gibco BRL, Livingston, Scotland) was added at the homogenisation step. The remaining details are as described above, except that ail the volumes were 50 fold less and the whole procedure was carried out in 400 μl Eppendorf tubes.

Example 2

Reverse Transcriptase Polymerase Chain Reaction (RT-PCR)

cDNA was synthesised from half the total RNA from each embryo using AMV reverse tranicriptase (Super RT, HT Biotech, Cambridge, UK). 3–5 micrograms of RNA was primed with oligo dT (Pharmacia), according to the manufacturers instructions for 60 minutes at 42° C. PCR amplification of the cDNA preparations was performed as previously described (sharkey, A. et al, *Molecular Endocrinol.*, 6: 1235–1241 (1992) with a Hybaid Omnigene DNA thermal cycler in a final volume of 30 μl using 1 U of Taq DNA polymerase (Cetus, Emeryville, Calif.) and 10 μM of each of the pair of external primers (see FIG. 4) in the manufacturer's recommended buffer. The following cycle profile was used: –30s at 95° C., 30s at X° C., 30s at 72° C. for 30 cycles, where X is the annealing temperature for each pair of cytokine primers.

|  | External Primers (° C.) | Internal Primers (° C.) |
|---|---|---|
| gp130 | 49 | 54 |
| HistRNA | 52 | 59 |

Oligonucleotide primers

Oligonucleotide primers for qp130 and HistidylRNA synthetase were synthesised on a Cruachem PS250 DNA synthesiser. Primer sequences were designed from published nucleotide sequences (see FIG. 4), such that amplification of any contaminating genomic DNA would result in a differently sizes product from the cDNA species.

Because of the small amount mate two pairs of primers were used for each target cDNA, in a nested PCR protocol. One thirtieth of the cDNA products were amplified using Amplitaq (Cetus), in the manufacturers recommended buffer. Following 30 cycles of PCR using the external primer pair, one fiftieth of the first round reaction was transferred to a fresh tube containing the inner primer pair, and subjected to a further 30 rounds of amplification. As negative control, an equal volume of the culture fluid in which the embryo was grown was extracted and subjected to RT-PCR in the same way. Also, 200 cells of the BeWo cell line (ECACC No 86082803) were extracted as positive control.

The primers used in this study are shown in FIG. 4, together with the size of the expected product. The identity of each product was confirmed by cloning and sequencing as described previously (Sharkey et al, *Mol. Endocrinol.* (1992)). To ensure that the product detected resulted from amplification of cDNA rather than contaminating genomic DNA, primers were chosen to cross intron/exon boundaries. Ten nanograms of genomic DNA was also subjected to PCR at the same time as the cDNA to verify no product of the expected size resulted from genomic DNA.

RESULTS

The technique of RT-PCR was applied to total RNA extracted from human embryos produced by in vitro fertilisation. Embryos were cultured to the appropriate stage, then quick-frozen in liquid nitrogen. Stored embryos were thawed and total RNA extracted. In order to produce detectable RT-PCR product from total RNA extracted from a single embryo, a nested PCR protocol was employed in which the cDNA was subjected to two sets of PCR amplification with an external primer pair, followed by an internal pair. Primers were based on published cDNA sequences and designed to span intron-exon boundaries so that amplification or contaminating genomic DNA could be readily distinguished from cDNA products.

Initially, cDNA from each embryo was tested with primers for histidyl tRNA synthetase (HistRS) to confirm successful RNA isolation and reverse transcription. The primers used gave rise to weak products of greater than 400 bp from genomic DNA and 110 bp from cDNA derived from HistRS mRNA. Transcripts for Heist RS were detected in mRNA from embryos at all stages of development, as well as in decidua and the choriocarcinoma cell line BeWo, used as positive controls (FIG. 3, lanes p and q respectively). No product was detected in an equal volume of embryo culture supernatant extracted and subjected to RT-PCR in the same way, indicating that there was no contamination of the culture with extraneous cDNA or RNA.

Examples of similar RT-PCR analysis with primers for gp130 are shown in FIG. 3. Stocks of cDNA were reverse transcribed from each RNA sample on two separate occasions and the PCR assays were repeated twice on each cDNA stock. The results are shown in FIG. 3, which displays the pattern of expression of gp130 during preimplantation development. The identity of the PCR fragment of the correct size was confirmed by sequencing of the cloned PCR product. In cases where novel sized products were seen, these were also cloned and sequenced.

For gp130, the predicted fragment is 712 bp. However, during the morula to blastocyst transition, a novel, smaller transcript was detected of approximately 600 bp. This result appeared consistent since, in sample j, which derives from cDNA made from 3 pooled blastocysts, both products were detected simultaneously. Upon cloning and sequencing, the smaller product appeared to arise due to an alternative splicing event which removes the exon encoding the transmembrane domain. The predicted sequence of the novel transcript is shown in FIGS. 1A–1D. The novel-splicing pattern also involves a frameshift, resulting in 45 new amino acids, before an in frame stop codon.

DISCUSSION

Many growth factors have been shown to influence the development of cultured preimplantation mammalian embryos (for review see Anderson, E. D., *J. Cellular Biochem.*, 53: 280–287 (1993) and Schultz, G. A. and Hevner, S., *Mutat. Res.*, 296: 17–31 (1992)).

However, there is good evidence for species to species differences in expression of growth factor receptors in preimplantation development. For instance, EGF mRNA is expressed in the pig embryo but has not been found at any stage in mouse preimplantation embryos (Vaughan et al, *Development*, 116: 663–669 (1992); Rapolee et al, *Science*, 241: 1823–1825 (1988); and Watson, A. J. et al, *Biol. Reprod.*, 50: 725–733 (1994)). Therefore the usefulness of these studies to researchers interested in factors controlling human preimplantation development is limited. In addition, the specific growth factors and receptors investigated in such studies frequently have been chosen on an ad hoc basis. Both or ethical and practical reasons, such an approach is not suitable for use with human embryos. We have therefore used a nested RT-PCR method which has allowed us to screen for the expression of growth factor and receptor mRNAs in single human preimplantation embryos. This method has been widely used over the last few years in other species since it is reliable, sensitive and economical in its use of embryo material.

RT-PCR with primers for Histidyl-tRNA synthetase was used on cDNA samples to confirm that cDNA had been successfully prepared from each embryo RNA sample. cDNA specific for this housekeeping gene was successfully detected in cDNA samples made even from a single 2-cell embryo, indicating that the method was sufficiently sensitive for this study.

We found that during the morula to blastocyst transition, the size of the gp130 PCR product decreased by about 100 bp. Sequencing of the smaller product indicated that it results from a novel splice variant of the gp130 mRNA. This new splice variant lacks the transmembrane domain, and would be expected to produce a novel form of gp130. Soluble gp130 protein has recently been detected in human serum and has been shown to antagonise the action of IL-6 and LIFR. When the cytokine's associate with their respective receptors, soluble gp130 is able to bind to this complex, blocking association with membrane bound gp130. The possibility is that selective expression of the novel gp130 in the blastocoel cavity in the late blastocyst stage would inactivate the effects of LIF in preventing differentiation of the linear cell mass, allowing ICM differentiation to proceed.

What is claimed is:

1. Isolated and substantially purified gp130 encoded by a DNA sequence as defined in SEQ ID NO:3 or having the amino acid sequence as defined in SEQ ID NO:4.

2. The purified gp130 of claim 1 encoded by a DNA sequence as defined in SEQ ID NO:3.

3. The purified gp130 of claim 1 having the amino acid sequence as defined in SEQ ID NO:4.

4. A pharmaceutical composition comprising gp130 as defined in claim 1 and a pharmaceutically acceptable excipient.

5. A method for treatment of a human pre-implantation embryo for conditions that can be treated by antagonizing the action of one or more growth factors selected from the group consisting of IL-6, LIF and Oncostatin M, comprising administering to the embryo gp130 as defined in claim 1 in the late blastocyst stage.

6. A method for antagonizing the action of one or more growth factors selected from the group consisting of IL-6, LIF and Oncostatin M, in a human pre-implantation embryo comprising administering to the embryo gp130 as defined in claim 1.

7. The method of claim 6, wherein said growth factor is IL-6.

8. The method of claim 6, wherein said growth factor is LIF.

9. The method of claim 6, wherein said growth factor is Oncostatin M.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 45 amino acids
      (B) TYPE: amino acid
      (C) STRANDEDNESS: single
      (D) TOPOLOGY: not relevant (ii) MOLECULE TYPE: peptide (xi) SEQUENCE DESCRIPTION: SEQ ID NO:1:

```
Glu Leu Lys Asn Thr Ser Gly Leu Met Phe Gln Ile Leu Gln Arg Val
1               5                   10                  15

Ile Leu Pro Ser Gly His Leu Thr Leu Leu Gln Gly Thr Ile Leu Ile
            20                  25                  30

Gln Lys Ile Lys Cys Ile Gln Met Ala Ile Ser Leu Met
        35                  40                  45
```

(2) INFORMATION FOR SEQ ID NO:2:

(i) SEQUENCE CHARACTERISTICS:
      (A) LENGTH: 138 base pairs
      (B) TYPE: nucleic acid
      (C) STRANDEDNESS: both
      (D) TOPOLOGY: linear (ii) MOLECULE TYPE: cDNA (xi) SEQUENCE DESCRIPTION: SEQ ID NO:2:

```
GAATTAAAAA ACACATCTGG CCTAATGTTC CAGATCCTTC AAAGAGTCAT ATTGCCCAGT      60

GGTCACCTCA CACTCCTCCA AGGCACAATT TTAATTCAAA AGATCAAATG TATTCAGATG     120

GCAATTTCAC TGATGTAA                                                   138
```

(2) INFORMATION FOR SEQ ID NO:3:

(i) SEQUENCE CHARACTERISTICS:
      (A) LENGTH: 1977 base pairs
      (B) TYPE: nucleic acid
      (C) STRANDEDNESS: both
      (D) TOPOLOGY: linear (ii) MOLECULE TYPE: cDNA (ix) FEATURE:
    (A) NAME/KEY: CDS
    (B) LOCATION: 1..1974

(xi) SEQUENCE DESCRIPTION: SEQ ID NO:3:

```
ATG TTG ACG TTG CAG ACT TGG GTA GTG CAA GCC TTG TTT ATT TTC CTC        48
Met Leu Thr Leu Gln Thr Trp Val Val Gln Ala Leu Phe Ile Phe Leu
 1               5                  10                  15

ACC ACT GAA TCT ACA GGT GAA CTT CTA GAT CCA TGT GGT TAT ATC AGT        96
Thr Thr Glu Ser Thr Gly Glu Leu Leu Asp Pro Cys Gly Tyr Ile Ser
             20                  25                  30

CCT GAA TCT CCA GTT GTA CAA CTT CAT TCT AAT TTC ACT GCA GTT TGT       144
Pro Glu Ser Pro Val Val Gln Leu His Ser Asn Phe Thr Ala Val Cys
         35                  40                  45

GTG CTA AAG GAA AAA TGT ATG GAT TAT TTT CAT GTA AAT GCT AAT TAC       192
Val Leu Lys Glu Lys Cys Met Asp Tyr Phe His Val Asn Ala Asn Tyr
     50                  55                  60

ATT GTC TGG AAA ACA AAC CAT TTT ACT ATT CCT AAG GAG CAA TAT ACT       240
Ile Val Trp Lys Thr Asn His Phe Thr Ile Pro Lys Glu Gln Tyr Thr
 65                  70                  75                  80

ATC ATA AAC AGA ACA GCA TCC AGT GTC ACC TTT ACA GAT ATA GCT TCA       288
Ile Ile Asn Arg Thr Ala Ser Ser Val Thr Phe Thr Asp Ile Ala Ser
                 85                  90                  95

TTA AAT ATT CAG CTC ACT TGC AAC ATT CTT ACA TTC GGA CAG CTT GAA       336
Leu Asn Ile Gln Leu Thr Cys Asn Ile Leu Thr Phe Gly Gln Leu Glu
            100                 105                 110

CAG AAT GTT TAT GGA ATC ACA ATA ATT TCA GGC TTG CCT CCA GAA AAA       384
Gln Asn Val Tyr Gly Ile Thr Ile Ile Ser Gly Leu Pro Pro Glu Lys
        115                 120                 125

CCT AAA AAT TTG AGT TGC ATT GTG AAC GAG GGG AAG AAA ATG AGG TGT       432
Pro Lys Asn Leu Ser Cys Ile Val Asn Glu Gly Lys Lys Met Arg Cys
    130                 135                 140

GAG TGG GAT GGT GGA AGG GAA ACA CAC TTG GAG ACA AAC TTC ACT TTA       480
Glu Trp Asp Gly Gly Arg Glu Thr His Leu Glu Thr Asn Phe Thr Leu
145                 150                 155                 160

AAA TCT GAA TGG GCA ACA CAC AAG TTT GCT GAT TGC AAA GCA AAA CGT       528
Lys Ser Glu Trp Ala Thr His Lys Phe Ala Asp Cys Lys Ala Lys Arg
                165                 170                 175

GAC ACC CCC ACC TCA TGC ACT GTT GAT TAT TCT ACT GTG TAT TTT GTC       576
Asp Thr Pro Thr Ser Cys Thr Val Asp Tyr Ser Thr Val Tyr Phe Val
            180                 185                 190

AAC ATT GAA GTC TGG GTA GAA GCA GAG AAT GCC CTT GGG AAG GTT ACA       624
Asn Ile Glu Val Trp Val Glu Ala Glu Asn Ala Leu Gly Lys Val Thr
        195                 200                 205

TCA GAT CAT ATC AAT TTT GAT CCT GTA TAT AAA GTG AAG CCC AAT CCG       672
Ser Asp His Ile Asn Phe Asp Pro Val Tyr Lys Val Lys Pro Asn Pro
    210                 215                 220

CCA CAT AAT TTA TCA GTG ATC AAC TCA GAG GAA CTG TCT AGT ATC TTA       720
Pro His Asn Leu Ser Val Ile Asn Ser Glu Glu Leu Ser Ser Ile Leu
225                 230                 235                 240

AAA TTG ACA TGG ACC AAC CCA AGT ATT AAG AGT GTT ATA ATA CTA AAA       768
Lys Leu Thr Trp Thr Asn Pro Ser Ile Lys Ser Val Ile Ile Leu Lys
                245                 250                 255

TAT AAC ATT CAA TAT AGG ACC AAA GAT GCC TCA ACT TGG AGC CAG ATT       816
Tyr Asn Ile Gln Tyr Arg Thr Lys Asp Ala Ser Thr Trp Ser Gln Ile
            260                 265                 270

CCT CCT GAA GAC ACA GCA TCC ACC CGA TCT TCA TTC ACT GTC CAA GAC       864
Pro Pro Glu Asp Thr Ala Ser Thr Arg Ser Ser Phe Thr Val Gln Asp
        275                 280                 285
```

```
CTT AAA CCT TTT ACA GAA TAT GTG TTT AGG ATT CGC TGT ATG AAG GAA        912
Leu Lys Pro Phe Thr Glu Tyr Val Phe Arg Ile Arg Cys Met Lys Glu
    290             295                 300

GAT GGT AAG GGA TAC TGG AGT GAC TGG AGT GAA GAA GCA AGT GGG ATC        960
Asp Gly Lys Gly Tyr Trp Ser Asp Trp Ser Glu Glu Ala Ser Gly Ile
305             310                 315                 320

ACC TAT GAA GAT AGA CCA TCT AAA GCA CCA AGT TTC TGG TAT AAA ATA       1008
Thr Tyr Glu Asp Arg Pro Ser Lys Ala Pro Ser Phe Trp Tyr Lys Ile
                325                 330                 335

GAT CCA TCC CAT ACT CAA GGC TAC AGA ACT GTA CAA CTC GTG TGG AAG       1056
Asp Pro Ser His Thr Gln Gly Tyr Arg Thr Val Gln Leu Val Trp Lys
            340                 345                 350

ACA TTG CCT CCT TTT GAA GCC AAT GGA AAA ATC TTG GAT TAT GAA GTG       1104
Thr Leu Pro Pro Phe Glu Ala Asn Gly Lys Ile Leu Asp Tyr Glu Val
        355                 360                 365

ACT CTC ACA AGA TGG AAA TCA CAT TTA CAA AAT TAC ACA GTT AAT GCC       1152
Thr Leu Thr Arg Trp Lys Ser His Leu Gln Asn Tyr Thr Val Asn Ala
    370                 375                 380

ACA AAA CTG ACA GTA AAT CTC ACA AAT GAT CGC TAT CTA GCA ACC CTA       1200
Thr Lys Leu Thr Val Asn Leu Thr Asn Asp Arg Tyr Leu Ala Thr Leu
385             390                 395                 400

ACA GTA AGA AAT CTT GTT GGC AAA TCA GAT GCA GCT GTT TTA ACT ATC       1248
Thr Val Arg Asn Leu Val Gly Lys Ser Asp Ala Ala Val Leu Thr Ile
                405                 410                 415

CCT GCC TGT GAC TTT CAA GCT ACT CAC CCT GTA ATG GAT CTT AAA GCA       1296
Pro Ala Cys Asp Phe Gln Ala Thr His Pro Val Met Asp Leu Lys Ala
                420                 425                 430

TTC CCC AAA GAT AAC ATG CTT TGG GTG GAA TGG ACT ACT CCA AGG GAA       1344
Phe Pro Lys Asp Asn Met Leu Trp Val Glu Trp Thr Thr Pro Arg Glu
            435                 440                 445

TCT GTA AAG AAA TAT ATA CTT GAG TGG TGT GTG TTA TCA GAT AAA GCA       1392
Ser Val Lys Lys Tyr Ile Leu Glu Trp Cys Val Leu Ser Asp Lys Ala
        450                 455                 460

CCC TGT ATC ACA GAC TGG CAA CAA GAA GAT GGT ACC GTG CAT CGC ACC       1440
Pro Cys Ile Thr Asp Trp Gln Gln Glu Asp Gly Thr Val His Arg Thr
465             470                 475                 480

TAT TTA AGA GGG AAC TTA GCA GAG AGC AAA TGC TAT TTG ATA ACA GTT       1488
Tyr Leu Arg Gly Asn Leu Ala Glu Ser Lys Cys Tyr Leu Ile Thr Val
                485                 490                 495

ACT CCA GTA TAT GCT GAT GGA CCA GGA AGC CCT GAA TCC ATA AAG GCA       1536
Thr Pro Val Tyr Ala Asp Gly Pro Gly Ser Pro Glu Ser Ile Lys Ala
                500                 505                 510

TAC CTT AAA CAA GCT CCA CCT TCC AAA GGA CCT ACT GTT CGG ACA AAA       1584
Tyr Leu Lys Gln Ala Pro Pro Ser Lys Gly Pro Thr Val Arg Thr Lys
            515                 520                 525

AAA GTA GGG AAA AAC GAA GCT GTC TTA GAG TGG GAC CAA CTT CCT GTT       1632
Lys Val Gly Lys Asn Glu Ala Val Leu Glu Trp Asp Gln Leu Pro Val
        530                 535                 540

GAT GTT CAG AAT GGA TTT ATC AGA AAT TAT ACT ATA TTT TAT AGA ACC       1680
Asp Val Gln Asn Gly Phe Ile Arg Asn Tyr Thr Ile Phe Tyr Arg Thr
545             550                 555                 560

ATC ATT GGA AAT GAA ACT GCT GTG AAT GTG GAT TCT TCC CAC ACA GAA       1728
Ile Ile Gly Asn Glu Thr Ala Val Asn Val Asp Ser Ser His Thr Glu
                565                 570                 575

TAT ACA TTG TCC TCT TTG ACT AGT GAC ACA TTG TAC ATG GTA CGA ATG       1776
Tyr Thr Leu Ser Ser Leu Thr Ser Asp Thr Leu Tyr Met Val Arg Met
            580                 585                 590

GCA GCA TAC ACA GAT GAA GGT GGG AAG GAT GGT CCA GAA TTC ACT TTT       1824
Ala Ala Tyr Thr Asp Glu Gly Gly Lys Asp Gly Pro Glu Phe Thr Phe
```

-continued

```
            595                 600                 605
ACT ACC CCA AAG TTT GAA TTA AAA AAC ACA TCT GGC CTA ATG TTC CAG        1872
Thr Thr Pro Lys Phe Glu Leu Lys Asn Thr Ser Gly Leu Met Phe Gln
        610                 615                 620

ATC CTT CAA AGA GTC ATA TTG CCC AGT GGT CAC CTC ACA CTC CTC CAA        1920
Ile Leu Gln Arg Val Ile Leu Pro Ser Gly His Leu Thr Leu Leu Gln
625                 630                 635                 640

GGC ACA ATT TTA ATT CAA AAG ATC AAA TGT ATT CAG ATG GCA ATT TCA        1968
Gly Thr Ile Leu Ile Gln Lys Ile Lys Cys Ile Gln Met Ala Ile Ser
                    645                 650                 655

CTG ATG TAA                                                            1977
Leu Met
```

(2) INFORMATION FOR SEQ ID NO:4:

(i) SEQUENCE CHARACTERISTICS:
        (A) LENGTH: 658 amino acids
        (B) TYPE: amino acid
        (D) TOPOLOGY: linear (ii) MOLECULE TYPE: protein (xi) SEQUENCE DESCRIPTION: SEQ ID NO:4:

```
Met Leu Thr Leu Gln Thr Trp Val Val Gln Ala Leu Phe Ile Phe Leu
 1               5                  10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270
```

```
Pro Pro Glu Asp Thr Ala Ser Thr Arg Ser Ser Phe Thr Val Gln Asp
            275                 280                 285
Leu Lys Pro Phe Thr Glu Tyr Val Phe Arg Ile Arg Cys Met Lys Glu
        290                 295                 300
Asp Gly Lys Gly Tyr Trp Ser Asp Trp Ser Glu Glu Ala Ser Gly Ile
305                 310                 315                 320
Thr Tyr Glu Asp Arg Pro Ser Lys Ala Pro Ser Phe Trp Tyr Lys Ile
                325                 330                 335
Asp Pro Ser His Thr Gln Gly Tyr Arg Thr Val Gln Leu Val Trp Lys
            340                 345                 350
Thr Leu Pro Pro Phe Glu Ala Asn Gly Lys Ile Leu Asp Tyr Glu Val
        355                 360                 365
Thr Leu Thr Arg Trp Lys Ser His Leu Gln Asn Tyr Thr Val Asn Ala
        370                 375                 380
Thr Lys Leu Thr Val Asn Leu Thr Asn Asp Arg Tyr Leu Ala Thr Leu
385                 390                 395                 400
Thr Val Arg Asn Leu Val Gly Lys Ser Asp Ala Ala Val Leu Thr Ile
                405                 410                 415
Pro Ala Cys Asp Phe Gln Ala Thr His Pro Val Met Asp Leu Lys Ala
            420                 425                 430
Phe Pro Lys Asp Asn Met Leu Trp Val Glu Trp Thr Thr Pro Arg Glu
        435                 440                 445
Ser Val Lys Lys Tyr Ile Leu Glu Trp Cys Val Leu Ser Asp Lys Ala
        450                 455                 460
Pro Cys Ile Thr Asp Trp Gln Gln Glu Asp Gly Thr Val His Arg Thr
465                 470                 475                 480
Tyr Leu Arg Gly Asn Leu Ala Glu Ser Lys Cys Tyr Leu Ile Thr Val
                485                 490                 495
Thr Pro Val Tyr Ala Asp Gly Pro Gly Ser Pro Glu Ser Ile Lys Ala
            500                 505                 510
Tyr Leu Lys Gln Ala Pro Pro Ser Lys Gly Pro Thr Val Arg Thr Lys
        515                 520                 525
Lys Val Gly Lys Asn Glu Ala Val Leu Glu Trp Asp Gln Leu Pro Val
        530                 535                 540
Asp Val Gln Asn Gly Phe Ile Arg Asn Tyr Thr Ile Phe Tyr Arg Thr
545                 550                 555                 560
Ile Ile Gly Asn Glu Thr Ala Val Asn Val Asp Ser Ser His Thr Glu
                565                 570                 575
Tyr Thr Leu Ser Ser Leu Thr Ser Asp Thr Leu Tyr Met Val Arg Met
            580                 585                 590
Ala Ala Tyr Thr Asp Glu Gly Gly Lys Asp Gly Pro Glu Phe Thr Phe
        595                 600                 605
Thr Thr Pro Lys Phe Glu Leu Lys Asn Thr Ser Gly Leu Met Phe Gln
        610                 615                 620
Ile Leu Gln Arg Val Ile Leu Pro Ser Gly His Leu Thr Leu Leu Gln
625                 630                 635                 640
Gly Thr Ile Leu Ile Gln Lys Ile Lys Cys Ile Gln Met Ala Ile Ser
                645                 650                 655
Leu Met
```

(2) INFORMATION FOR SEQ ID NO:5:

(i) SEQUENCE CHARACTERISTICS:

(A) LENGTH: 2754 base pairs
(B) TYPE: nucleic acid
(C) STRANDEDNESS: both
(D) TOPOLOGY: linear (ii) MOLECULE TYPE: cDNA (ix) FEATURE:
(A) NAME/KEY: CDS
(B) LOCATION: 1..2754

(xi) SEQUENCE DESCRIPTION: SEQ ID NO:5:

```
ATG TTG ACG TTG CAG ACT TGG GTA GTG CAA GCC TTG TTT ATT TTC CTC        48
Met Leu Thr Leu Gln Thr Trp Val Val Gln Ala Leu Phe Ile Phe Leu
  1               5                  10                  15

ACC ACT GAA TCT ACA GGT GAA CTT CTA GAT CCA TGT GGT TAT ATC AGT        96
Thr Thr Glu Ser Thr Gly Glu Leu Leu Asp Pro Cys Gly Tyr Ile Ser
             20                  25                  30

CCT GAA TCT CCA GTT GTA CAA CTT CAT TCT AAT TTC ACT GCA GTT TGT       144
Pro Glu Ser Pro Val Val Gln Leu His Ser Asn Phe Thr Ala Val Cys
         35                  40                  45

GTG CTA AAG GAA AAA TGT ATG GAT TAT TTT CAT GTA AAT GCT AAT TAC       192
Val Leu Lys Glu Lys Cys Met Asp Tyr Phe His Val Asn Ala Asn Tyr
 50                  55                  60

ATT GTC TGG AAA ACA AAC CAT TTT ACT ATT CCT AAG GAG CAA TAT ACT       240
Ile Val Trp Lys Thr Asn His Phe Thr Ile Pro Lys Glu Gln Tyr Thr
 65                  70                  75                  80

ATC ATA AAC AGA ACA GCA TCC AGT GTC ACC TTT ACA GAT ATA GCT TCA       288
Ile Ile Asn Arg Thr Ala Ser Ser Val Thr Phe Thr Asp Ile Ala Ser
                 85                  90                  95

TTA AAT ATT CAG CTC ACT TGC AAC ATT CTT ACA TTC GGA CAG CTT GAA       336
Leu Asn Ile Gln Leu Thr Cys Asn Ile Leu Thr Phe Gly Gln Leu Glu
            100                 105                 110

CAG AAT GTT TAT GGA ATC ACA ATA ATT TCA GGC TTG CCT CCA GAA AAA       384
Gln Asn Val Tyr Gly Ile Thr Ile Ile Ser Gly Leu Pro Pro Glu Lys
        115                 120                 125

CCT AAA AAT TTG AGT TGC ATT GTG AAC GAG GGG AAG AAA ATG AGG TGT       432
Pro Lys Asn Leu Ser Cys Ile Val Asn Glu Gly Lys Lys Met Arg Cys
130                 135                 140

GAG TGG GAT GGT GGA AGG GAA ACA CAC TTG GAG ACA AAC TTC ACT TTA       480
Glu Trp Asp Gly Gly Arg Glu Thr His Leu Glu Thr Asn Phe Thr Leu
145                 150                 155                 160

AAA TCT GAA TGG GCA ACA CAC AAG TTT GCT GAT TGC AAA GCA AAA CGT       528
Lys Ser Glu Trp Ala Thr His Lys Phe Ala Asp Cys Lys Ala Lys Arg
                165                 170                 175

GAC ACC CCC ACC TCA TGC ACT GTT GAT TAT TCT ACT GTG TAT TTT GTC       576
Asp Thr Pro Thr Ser Cys Thr Val Asp Tyr Ser Thr Val Tyr Phe Val
            180                 185                 190

AAC ATT GAA GTC TGG GTA GAA GCA GAG AAT GCC CTT GGG AAG GTT ACA       624
Asn Ile Glu Val Trp Val Glu Ala Glu Asn Ala Leu Gly Lys Val Thr
        195                 200                 205

TCA GAT CAT ATC AAT TTT GAT CCT GTA TAT AAA GTG AAG CCC AAT CCG       672
Ser Asp His Ile Asn Phe Asp Pro Val Tyr Lys Val Lys Pro Asn Pro
    210                 215                 220

CCA CAT AAT TTA TCA GTG ATC AAC TCA GAG GAA CTG TCT AGT ATC TTA       720
Pro His Asn Leu Ser Val Ile Asn Ser Glu Glu Leu Ser Ser Ile Leu
225                 230                 235                 240

AAA TTG ACA TGG ACC AAC CCA AGT ATT AAG AGT GTT ATA ATA CTA AAA       768
Lys Leu Thr Trp Thr Asn Pro Ser Ile Lys Ser Val Ile Ile Leu Lys
                245                 250                 255

TAT AAC ATT CAA TAT AGG ACC AAA GAT GCC TCA ACT TGG AGC CAG ATT       816
Tyr Asn Ile Gln Tyr Arg Thr Lys Asp Ala Ser Thr Trp Ser Gln Ile
```

```
                        260                    265                   270
CCT CCT GAA GAC ACA GCA TCC ACC CGA TCT TCA TTC ACT GTC CAA GAC         864
Pro Pro Glu Asp Thr Ala Ser Thr Arg Ser Ser Phe Thr Val Gln Asp
            275                    280                    285

CTT AAA CCT TTT ACA GAA TAT GTG TTT AGG ATT CGC TGT ATG AAG GAA         912
Leu Lys Pro Phe Thr Glu Tyr Val Phe Arg Ile Arg Cys Met Lys Glu
            290                    295                    300

GAT GGT AAG GGA TAC TGG AGT GAC TGG AGT GAA GAA GCA AGT GGG ATC         960
Asp Gly Lys Gly Tyr Trp Ser Asp Trp Ser Glu Glu Ala Ser Gly Ile
305                    310                    315                    320

ACC TAT GAA GAT AGA CCA TCT AAA GCA CCA AGT TTC TGG TAT AAA ATA        1008
Thr Tyr Glu Asp Arg Pro Ser Lys Ala Pro Ser Phe Trp Tyr Lys Ile
            325                    330                    335

GAT CCA TCC CAT ACT CAA GGC TAC AGA ACT GTA CAA CTC GTG TGG AAG        1056
Asp Pro Ser His Thr Gln Gly Tyr Arg Thr Val Gln Leu Val Trp Lys
            340                    345                    350

ACA TTG CCT CCT TTT GAA GCC AAT GGA AAA ATC TTG GAT TAT GAA GTG        1104
Thr Leu Pro Pro Phe Glu Ala Asn Gly Lys Ile Leu Asp Tyr Glu Val
            355                    360                    365

ACT CTC ACA AGA TGG AAA TCA CAT TTA CAA AAT TAC ACA GTT AAT GCC        1152
Thr Leu Thr Arg Trp Lys Ser His Leu Gln Asn Tyr Thr Val Asn Ala
            370                    375                    380

ACA AAA CTG ACA GTA AAT CTC ACA AAT GAT CGC TAT CTA GCA ACC CTA        1200
Thr Lys Leu Thr Val Asn Leu Thr Asn Asp Arg Tyr Leu Ala Thr Leu
385                    390                    395                    400

ACA GTA AGA AAT CTT GTT GGC AAA TCA GAT GCA GCT GTT TTA ACT ATC        1248
Thr Val Arg Asn Leu Val Gly Lys Ser Asp Ala Ala Val Leu Thr Ile
            405                    410                    415

CCT GCC TGT GAC TTT CAA GCT ACT CAC CCT GTA ATG GAT CTT AAA GCA        1296
Pro Ala Cys Asp Phe Gln Ala Thr His Pro Val Met Asp Leu Lys Ala
            420                    425                    430

TTC CCC AAA GAT AAC ATG CTT TGG GTG GAA TGG ACT ACT CCA AGG GAA        1344
Phe Pro Lys Asp Asn Met Leu Trp Val Glu Trp Thr Thr Pro Arg Glu
            435                    440                    445

TCT GTA AAG AAA TAT ATA CTT GAG TGG TGT GTG TTA TCA GAT AAA GCA        1392
Ser Val Lys Lys Tyr Ile Leu Glu Trp Cys Val Leu Ser Asp Lys Ala
            450                    455                    460

CCC TGT ATC ACA GAC TGG CAA CAA GAA GAT GGT ACC GTG CAT CGC ACC        1440
Pro Cys Ile Thr Asp Trp Gln Gln Glu Asp Gly Thr Val His Arg Thr
465                    470                    475                    480

TAT TTA AGA GGG AAC TTA GCA GAG AGC AAA TGC TAT TTG ATA ACA GTT        1488
Tyr Leu Arg Gly Asn Leu Ala Glu Ser Lys Cys Tyr Leu Ile Thr Val
            485                    490                    495

ACT CCA GTA TAT GCT GAT GGA CCA GGA AGC CCT GAA TCC ATA AAG GCA        1536
Thr Pro Val Tyr Ala Asp Gly Pro Gly Ser Pro Glu Ser Ile Lys Ala
            500                    505                    510

TAC CTT AAA CAA GCT CCA CCT TCC AAA GGA CCT ACT GGT CGG ACA AAA        1584
Tyr Leu Lys Gln Ala Pro Pro Ser Lys Gly Pro Thr Gly Arg Thr Lys
            515                    520                    525

AAA GTA GGG AAA AAC GAA GCT GTC TTA GAG TGG GAC CAA CTT CCT GTT        1632
Lys Val Gly Lys Asn Glu Ala Val Leu Glu Trp Asp Gln Leu Pro Val
            530                    535                    540

GAT GTT CAG AAT GGA TTT ATC AGA AAT TAT ACT ATA TTT TAT AGA ACC        1680
Asp Val Gln Asn Gly Phe Ile Arg Asn Tyr Thr Ile Phe Tyr Arg Thr
545                    550                    555                    560

ATC ATT GGA AAT GAA ACT GCT GTG AAT GTG GAT TCT TCC CAC ACA GAA        1728
Ile Ile Gly Asn Glu Thr Ala Val Asn Val Asp Ser Ser His Thr Glu
            565                    570                    575

TAT ACA TTG TCC TCT TTG ACT AGT GAC ACA TTG TAC ATG GTA CGA ATG        1776
```

```
Tyr Thr Leu Ser Ser Leu Thr Ser Asp Thr Leu Tyr Met Val Arg Met
            580                 585                 590

GCA GCA TAC ACA GAT GAA GGT GGG AAG GAT GGT CCA GAA TTC ACT TTT     1824
Ala Ala Tyr Thr Asp Glu Gly Gly Lys Asp Gly Pro Glu Phe Thr Phe
        595                 600                 605

ACT ACC CCA AAG TTT GCT CAA GGA GAA ATT GAA GCC ATA GTC GTG CCT     1872
Thr Thr Pro Lys Phe Ala Gln Gly Glu Ile Glu Ala Ile Val Val Pro
610                 615                 620

GTT TGC TTA GCA TTC CTA TTG ACA ACT CTT CTG GGA GTG CTG TTC TGC     1920
Val Cys Leu Ala Phe Leu Leu Thr Thr Leu Leu Gly Val Leu Phe Cys
625                 630                 635                 640

TTT AAT AAG CGA GAC CTA ATT AAA AAA CAC ATC TGG CCT AAT GTT CCA     1968
Phe Asn Lys Arg Asp Leu Ile Lys Lys His Ile Trp Pro Asn Val Pro
                645                 650                 655

GAT CCT TCA AAG AGT CAT ATT GCC CAG TGG TCA CCT CAC ACT CCT CCA     2016
Asp Pro Ser Lys Ser His Ile Ala Gln Trp Ser Pro His Thr Pro Pro
            660                 665                 670

AGG CAC AAT TTT AAT TCA AAA GAT CAA ATG TAT TCA GAT GGC AAT TTC     2064
Arg His Asn Phe Asn Ser Lys Asp Gln Met Tyr Ser Asp Gly Asn Phe
        675                 680                 685

ACT GAT GTA AGT GTT GTG GAA ATA GAA GCA AAT GAC AAA AAG CCT TTT     2112
Thr Asp Val Ser Val Val Glu Ile Glu Ala Asn Asp Lys Lys Pro Phe
    690                 695                 700

CCA GAA GAT CTG AAA TCA TTG GAC CTG TTC AAA AAG GAA AAA ATT AAT     2160
Pro Glu Asp Leu Lys Ser Leu Asp Leu Phe Lys Lys Glu Lys Ile Asn
705                 710                 715                 720

ACT GAA GGA CAC AGC AGT GGT ATT GGG GGT TCT TCA TGC ATG TCA TCT     2208
Thr Glu Gly His Ser Ser Gly Ile Gly Gly Ser Ser Cys Met Ser Ser
                725                 730                 735

TCT AGG CCA AGC ATT TCT AGC AGT GAT GAA AAT GAA TCT TCA CAA AAC     2256
Ser Arg Pro Ser Ile Ser Ser Ser Asp Glu Asn Glu Ser Ser Gln Asn
            740                 745                 750

ACT TCG AGC ACT GTC CAG TAT TCT ACC GTG GTA CAC AGT GGC TAC AGA     2304
Thr Ser Ser Thr Val Gln Tyr Ser Thr Val Val His Ser Gly Tyr Arg
        755                 760                 765

CAC CAA GTT CCG TCA GTC CAA GTC TTC TCA AGA TCC GAG TCT ACC CAG     2352
His Gln Val Pro Ser Val Gln Val Phe Ser Arg Ser Glu Ser Thr Gln
    770                 775                 780

CCC TTG TTA GAT TCA GAG GAG CGG CCA GAA GAT CTA CAA TTA GTA GAT     2400
Pro Leu Leu Asp Ser Glu Glu Arg Pro Glu Asp Leu Gln Leu Val Asp
785                 790                 795                 800

CAT GTA GAT GGC GGT GAT GGT ATT TTG CCC AGG CAA CAG TAC TTC AAA     2448
His Val Asp Gly Gly Asp Gly Ile Leu Pro Arg Gln Gln Tyr Phe Lys
                805                 810                 815

CAG AAC TGC AGT CAG CAT GAA TCC AGT CCA GAT ATT TCA CAT TTT GAA     2496
Gln Asn Cys Ser Gln His Glu Ser Ser Pro Asp Ile Ser His Phe Glu
            820                 825                 830

AGG TCA AAG CAA GTT TCA TCA GTC AAT GAG GAA GAT TTT GTT AGA CTT     2544
Arg Ser Lys Gln Val Ser Ser Val Asn Glu Glu Asp Phe Val Arg Leu
        835                 840                 845

AAA CAG CAG ATT TCA GAT CAT ATT TCA CAA TCC TGT GGA TCT GGG CAA     2592
Lys Gln Gln Ile Ser Asp His Ile Ser Gln Ser Cys Gly Ser Gly Gln
    850                 855                 860

ATG AAA ATG TTT CAG GAA GTT TCT GCA GCA GAT GCT TTT GGT CCA GGT     2640
Met Lys Met Phe Gln Glu Val Ser Ala Ala Asp Ala Phe Gly Pro Gly
865                 870                 875                 880

ACT GAG GGA CAA GTA GAA AGA TTT GAA ACA GTT GGC ATG GAG GCT GCG     2688
Thr Glu Gly Gln Val Glu Arg Phe Glu Thr Val Gly Met Glu Ala Ala
                885                 890                 895
```

```
ACT GAT GAA GGC ATG CCT AAA AGT TAC TTA CCA CAG ACT GTA CGG CAA    2736
Thr Asp Glu Gly Met Pro Lys Ser Tyr Leu Pro Gln Thr Val Arg Gln
            900             905             910

GGC GGC TAC ATG CCT CAG                                            2754
Gly Gly Tyr Met Pro Gln
        915
```

(2) INFORMATION FOR SEQ ID NO:6:

(i) SEQUENCE CHARACTERISTICS:
        (A) LENGTH: 918 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Thr Leu Gln Thr Trp Val Val Gln Ala Leu Phe Ile Phe Leu
 1               5                  10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320
```

-continued

```
Thr Tyr Glu Asp Arg Pro Ser Lys Ala Pro Ser Phe Trp Tyr Lys Ile
            325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
            370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
            405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
            450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
            485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Gly Arg Thr Lys
            515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
            565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
            610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
            645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
            675                 680                 685

Thr Asp Val Ser Val Val Glu Ile Glu Ala Asn Asp Lys Lys Pro Phe
            690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
            725                 730                 735
```

```
Ser Arg Pro Ser Ile Ser Ser Asp Glu Asn Glu Ser Ser Gln Asn
        740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
        770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
                820                 825                 830

Arg Ser Lys Gln Val Ser Ser Val Asn Glu Glu Asp Phe Val Arg Leu
                835                 840                 845

Lys Gln Gln Ile Ser Asp His Ile Ser Gln Ser Cys Gly Ser Gly Gln
                850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
                900                 905                 910

Gly Gly Tyr Met Pro Gln
            915
```

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:7:

CCGCAGGTCG AGACAGC                          17

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:8:

CAAACACCTT CTCGCGAA                         18

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:9:

```
CTTCAGGGAG AGCGCGTGC                                                19

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:10:

TCATCAGGAC CCAGCTGTGC                                               20

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:11:

TTGACTAGTG ACACATTGTA C                                             21

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:12:

TGAAACTTGC TTTGACCTTT                                               20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:13:

GGTACGAATG GCAGCATACA                                               20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:14:

CTGGACTGGA TTCATGCTGA                                               20
```